United States Patent [19]

Kirchhoff et al.

[11] Patent Number: 5,145,953

[45] Date of Patent: Sep. 8, 1992

[54] MONOMERS OF BISCYCLOBUTARENES BRIDGED BY AT LEAST ONE AZO LINKAGE

[75] Inventors: Robert A. Kirchhoff, Midland, Mich.; Alan K. Schrock, Lake Jackson, Tex.

[73] Assignee: The Dow Chemical Company, Midland, Mich.

[21] Appl. No.: 151,682

[22] Filed: Feb. 2, 1988

[51] Int. Cl.$^5$ ............... C07C 245/08; C07C 245/10; C09B 29/01

[52] U.S. Cl. ................. 534/851; 526/218.1; 526/219; 526/219.1; 534/659; 534/805; 534/806; 534/809; 534/821; 534/829; 534/832; 534/833; 534/840; 534/849; 534/850; 534/573; 564/328

[58] Field of Search ............... 534/659, 840, 832, 829, 534/806, 805, 809, 851, 833, 821, 573, 849, 850

[56] References Cited

U.S. PATENT DOCUMENTS 4,540,763  9/1985  Kirchhoff ..................... 526/281
4,687,823  8/1987  Kirchhoff et al. ............. 526/284

OTHER PUBLICATIONS

Brand et al, Chemical Abstracts, vol. 29, #2930$^9$ to 2931$^5$ (1935).

*Primary Examiner*—Floyd D. Higel
*Attorney, Agent, or Firm*—J. H. Roberts; C. J. Enright

[57] ABSTRACT

A biscyclobutarene monomer is prepared having two cyclobutarene moieties bridged by a divalent radical having at least one azo linkage. The monomers can be polymerized to form polymers exhibiting outstanding thermooxidative stability at high temperatures for prolonged time periods.

6 Claims, 2 Drawing Sheets

MONOMERS OF BISCYCLOBUTARENES BRIDGED BY AT LEAST ONE AZO LINKAGE

The U.S. Government has a paid-up license in this invention and the right in limited circumstances to require the patent owner to license others on reasonable terms as provided for by the terms of Contract No. F33615-85-C-5092 awarded by Wright-Patterson Air Force Base.

BACKGROUND OF THE INVENTION

This invention relates to monomers and oligomers of biscyclobutarenes and polymers derived therefrom. More specifically, it relates to monomers, oligomers, and polymers of biscyclobutarenes that are bridged by at least one azo linkage.

Polymers derived from biscyclobutarene monomers are disclosed in U.S. Pat. No. 4,540,763. The polymers are prepared by subjecting biscyclobutarene monomers to temperatures sufficient for polymerization. The polymers exhibit excellent thermal stability at high temperatures, good chemical resistance to most industrial solvents, good physical and mechanical properties, and low sensitivity to water. The polymers are useful for preparing composites, coatings and films; and as adhesives.

Although the polymers of U.S. Pat. No. 4,540,763 exhibit excellent thermal stability at high temperatures, numerous applications in high performance industries, such as the aerospace industry, require polymers for advanced composites that not only exhibit high temperature thermal stability but also exhibit high temperature thermal stability in air for prolonged time periods. Unfortunately, many of the polymers of U.S. Pat. No. 4,540,763 do not exhibit the long term thermooxidative stability required for high performance applications. The polyvalent organic and inorganic bridging groups of the biscyclobutarenes are susceptible to oxidation reactions when subjected to elevated temperatures for extended times. Particularly susceptible are aliphatic bridging groups.

In view of the deficiencies of the prior art, it would be desirable to prepare polymers derived from biscyclobutarene monomers and oligomers that exhibit outstanding thermooxidative stability for prolonged time periods.

SUMMARY OF THE INVENTION

In one aspect, the invention is a biscyclobutarene monomer and a biscyclobutarene oligomer derived therefrom. The biscyclobutarene monomer comprises two cyclobutarene moieties bridged by a divalent radical having at least one azo linkage. The biscyclobutarene oligomer comprises the reaction product of an amino-substituted cyclobutarene and at least one diamine.

In another aspect, the invention comprises a process for preparing a polymer from the biscyclobutarene monomer or the biscyclobutarene oligomer of this invention. The process comprises the step of subjecting the monomer or oligomer to ring scission polymerization conditions.

The polymers derived from the biscyclobutarene monomers and the biscyclobutarene oligomers exhibit excellent thermooxidative stability at high temperatures for prolonged time periods. The azo linkage of the divalent radical contributes to the thermooxidative stability of the bridging member, and therefore the thermooxidative stability of the polymer is enhanced. The polymers are useful as matrix resins for advanced composites and as high performance adhesives for bonding substrates. They are also useful for any other application requiring service in a harsh environment.

DETAILED DESCRIPTION OF THE INVENTION

Figure 1:
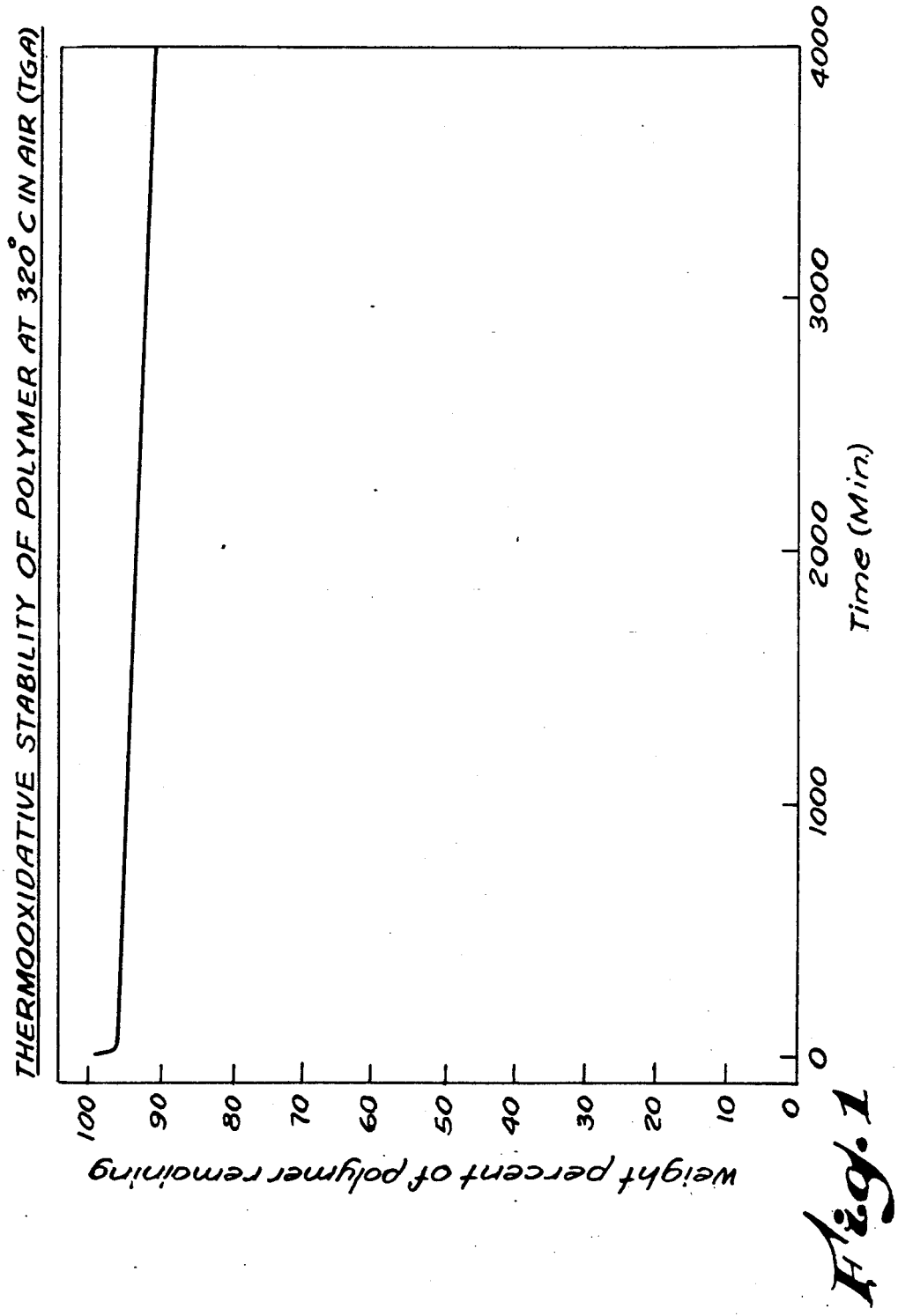
FIGS. 1 and 2 are graphs of the thermooxidative stability of a polymer derived from a preferred monomer of this invention.

For purposes of describing this invention, a cyclobutarene is a substituted or unsubstituted aromatic compound to which is fused one or more cyclobutane rings or one or more substituted cyclobutane rings. The aromatic ring of the cyclobutarene can be substituted with nitro, chloro, bromo, or any other group that will not adversely affect the thermooxidative stability of the polymers derived from the monomers of this invention. Likewise, the cyclobutane ring can be substituted with similar thermooxidatively stable groups. The most preferred cyclobutarene is benzocyclobutene.

The monomers of this invention are biscyclobutarene monomers. The cyclobutarene moieties of the monomer are bridged by a divalent radical that has at least one azo linkage. In one embodiment of this invention, one azo linkage bridges the cyclobutarene moieties and the monomer has the formula:

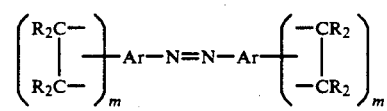

wherein
Ar is an aromatic moiety having one valence on each of two adjacent carbon atoms of an aromatic ring;
each R is independently hydrogen, a monovalent electron donating moiety, or a monovalent electron withdrawing moiety; and
m is an integer of 1 or 2.

Suitable aromatic moieties are derived from benzene, naphthalene, phenanthrene, anthracene, biphenyl, and two or more aromatic moieties bridged by alkylene, cycloalkylene, oxygen, nitrogen, sulfoxide, sulfone, or carbonyl moieties. Also included are aromatic moieties derived from substituted aromatic compounds, such as, for example, lower alkyl, halo, nitro, alkoxy and aryloxy-substituted aromatic compounds; and moieties derived from hetercyclic compounds, such as pyridine and picoline.

The aromatic moiety has one valence on each of two adjacent carbon atoms of an aromatic ring so that a substituted or unsubstituted cyclobutane ring can fuse to the aromatic ring. When the subscript m of the formula is 2, then the aromatic moiety has one valence on each carbon atom in two separate pairs of adjacent carbon atoms of one or more aromatic rings. In this instance, a substituted or unsubstituted cyclobutane ring fuses to each of the two separate pairs of adjacent carbon atoms.

Monovalent electron-donating moieties are either monovalent atoms or monovalent radicals which donate electrons more than a hydrogen atom would if accompanying the same site. Monovalent electron-withdrawing moieties are either atoms or radicals which more readily withdraw an electron relative to a hydrogen atom. Examples of suitable electron-withdrawing moieties include nitro, cyano, bromo, iodo, chloro, fluoro, and carboxy. Examples of suitable electron-donating moieties include lower alkyl, aryl, hydroxy, alkoxy, and aryloxy.

Preferably, the cyclobutarene moieties are benzocyclobutene moieties and the monomer has the formula:

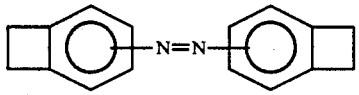
(I)

In another embodiment of this invention, the azo linkage per se is a diarylene-substituted azo linkage. As the term is used herein, an arylene is a divalent aromatic moiety. The diarylene-substituted azo linkage has the following formula:

wherein Ar is arylene.

In one embodiment, the divalent radical has one diarylene-substituted azo linkage and the monomer has the formula:

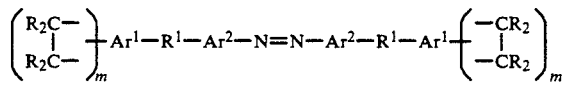

wherein
Ar$^1$ is an aromatic moiety having one valence on each of two adjacent carbon atoms of an aromatic ring;
Ar$^2$ is arylene;
each R is independently hydrogen, a monovalent electron-donating moiety, or a monovalent electron withdrawing moiety;
R$^1$ is a direct bond, oxygen, sulfur, sulfinyl

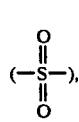

sulfonyl

carbonyl

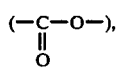

vinylene (—C=C—), ethynylene (—C≡C—), oxycarbonyl (—C—O—),
‖
O aminocarbonyl

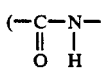

or

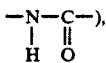

or fluoroalkylene (—(CF$_2$)$_n$—); and
m is an integer of 1 or 2.

A preferred monomer has the following formula:

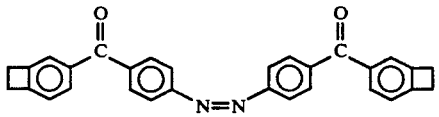
(II)

The monomers of this invention are prepared by the oxidative coupling reaction of an amino-substituted cyclobutarene with itself. Process conditions for oxidative coupling reactions are disclosed in Bach, *Polymer Preprints*, 7, 576, (1966), and are suitable here. A catalytic amount of cuprous chloride is dissolved in a suitable dried solvent, such as pyridine, and sparged with a sufficient quantity of air to form a copper/solvent complex. The amino-substituted cyclobutarene is then added is then added while the air sparging is continued. When the oxidative coupling reaction is complete, the reaction mixture is contacted with water and the aqueous phase is separated from the remaining reaction mixture. The biscyclobutarene monomer can then be extracted from the aqueous phase with a suitable solvent, such as methylene chloride.

Processes known in the art can be used to prepare amino-substituted cyclobutarenes. Copending U.S. application Ser. No. 27,470, filed Mar. 18, 1987, now abandoned, discloses the preparation of a preferred amino-substituted cyclobutarene of the formula:

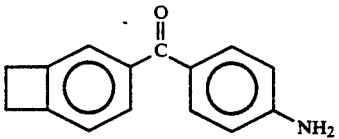
(III)

Amino-substituted cyclobutarenes can be prepared by selectively reducing the nitro group of a nitro-substituted cyclobutarene. The reduction can be carried out by hydrogenation over a noble metal catalyst, such as palladium metal or palladium oxide, as described in Rylander, *Catalytic Hydrogenation in Organic Syntheses*, pp. 114, Academic Press, (1979).

Lloyd et al., *Tetrahedron*, 20, 2185, (1964), and Horner et al., *Chem. Ber.*, 93, 1774, (1960), disclose a process for preparing 4-nitrobenzocyclobutene via the nitration of benzocyclobutene. Similarly, other nitrocyclobutarenes can be prepared via the nitration of the corresponding cyclobutarene.

Other nitro-substituted cyclobutarenes can be prepared by the processes disclosed in Heck, *Palladium Reagents in Organic Syntheses*, Academic Press, (1985); Sandler, *Organic Functional Group Preparations*, 2nd ed., Academic Press, (1983); and Bacon et al., *J. of the Chem. Soc.*, 4953, (1965).

Heck discloses palladium-catalyzed reactions of aryl bromides with aryl iodides, vinyl aromatic compounds, acetenyl aromatic compounds, and thio-substituted aromatic compounds. The reaction of an aryl bromide with an aryl iodide yields a biaryl compound. This process can be used, for example, to react 4-bromobenzocyclobutene with 4-nitroiodobenzene to yield a compound of the formula:

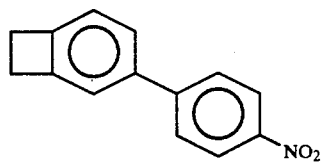

The reaction of an aryl bromide with a vinyl aromatic compound yields a diaryl-substituted olefin. This process can be used, for example, to react 4-bromobenzocyclobutene with 4-nitrostyrene to yield a compound of the formula:

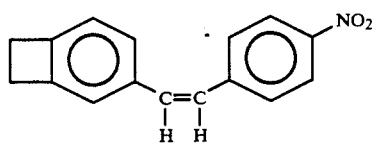

Similarly, the reaction of 4-bromobenzocyclobutene with 4-nitrophenylacetylene yields a compound of the formula:

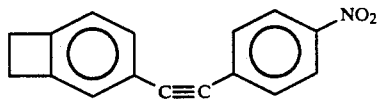

The reaction of 4-bromobenzocyclobutene with 4-nitrobenzenethiol yields a sulfide of the formula:

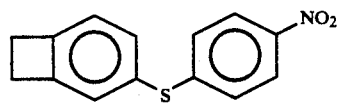

Sandler discloses the oxidation of a sulfide to a sulfoxide with hydrogen peroxide and the oxidation of a sulfide to a sulfone with a peracid. These processes can be used to oxidize the sulfide disclosed hereinbefore to yield compounds of the formulae:

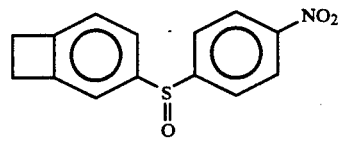

-continued

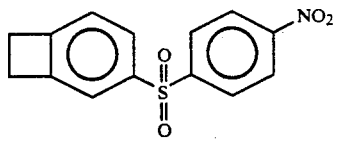

Sandler also discloses reactions of aryl acids with aryl amines and phenols. The reaction of an aryl acid with the aryl amine yields an aryl amide. This process can be used, for example, to react benzocyclobutene-4-carboxylic acid with 4-nitroaniline to yield a compound of the formula:

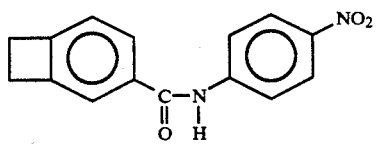

The reaction of an aryl acid or an aryl acid chloride with a phenol yields an aryl ester. If benzocyclobutene-4-carboxylic acid choride is reacted with 4-nitrophenol, then the reaction will yield a compound of the formula:

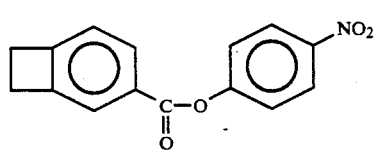

Bacon et al. discloses the reaction of aryl bromides with phenols in the presence of cuprous oxide and dimethylacetamide to prepare aryl ethers. This process can be used, for example, to react 4-bromobenzocyclobutene with 4-nitrophenol to yield a compound of the formula:

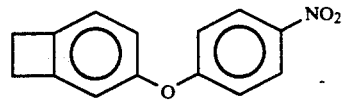

In another embodiment of this invention, reactive biscyclobutarene oligomers are prepared by reacting an amino-substituted cyclobutarene with at least one diamine. The reaction is an oxidative coupling reaction between the amino-substituted cyclobutarene and the diamine similar to the oxidative coupling reaction of the amino-substituted cyclobutarene with itself, as described hereinbefore. The oxidative coupling reaction forms a reactive biscyclobutarene oligomer bridged by a divalent radical having a plurality of azo linkages. Suitable diamines include dianilines, such as oxydianiline, sulphonyl dianiline, thiodianiline, and 2,2-perfluoropropyldianiline; and aryl diamines such as phenylene diamine, naphthylene diamine, and benzidine. In one embodiment, the reactive biscyclobutarene oligomer has the following formula:

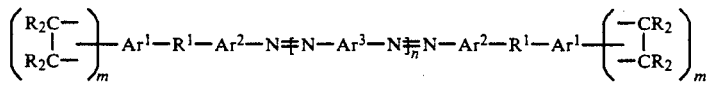

wherein

Ar$^1$, Ar$^2$, R, R$^1$, and m are defined as previously defined hereinbefore;

Ar$^3$ is arylene; and n is an integer of 1 or more, preferably an integer between 1 and 1000, inclusive.

As an example of the reaction between the amino-substituted cyclobutarene and the diamine, the oxidative coupling of 4-amino-benzocyclobutene with oxydianiline will yield a reactive oligomer of the formula:

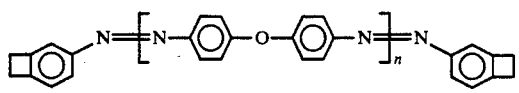

wherein n is an integer of 1 or more, preferably an integer between 1 and 1000, inclusive.

A preferred example of this reaction is the oxidative coupling of the amino-substituted cyclobutarene disclosed as Formula III with oxydianiline to yield a reactive oligomer of the formula:

butane ring or a moiety capable of reacting with an opened cyclobutane ring.

When the cyclobutane ring of the cyclobutarene moiety opens, it forms a conjugated diene (orthoquinodimethane) that can react with a dienophilic moiety (a "diene loving" moiety). Typically, the opened ring reacts with another opened ring. U.S. Pat. No. 4,540,763 discloses some of the potential reactions that can occur when opened rings react with each other. Also, an opened ring can potentially react with an olefinic or acetylenic moiety via a Diels-Alder reaction as disclosed in Feiser and Feiser, *Organic Chemistry*, 3rd ed., 1980.

The cyclobutane ring of the cyclobutarene moiety can open by subjecting the monomers and reactive oligomers to sufficient heat. Typically, temperatures from about 200° C. to 300° C. are sufficient to open the ring. Polymerization solvents or catalysts are unnecessary, although a copper salt catalyst may lower the required temperature. Gamma radiation and electron beam radiation can also open the ring, but thermal radiation is preferred since it can be applied by conventional

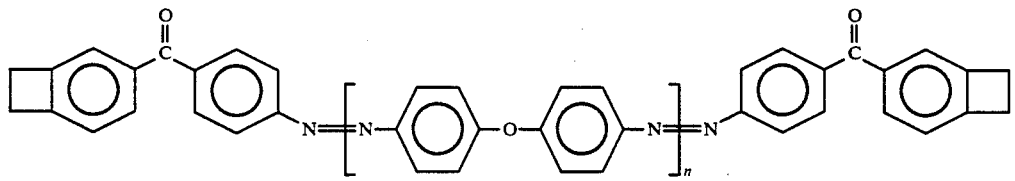

wherein n is an integer of 1 or more, preferably an interger between 1 and 1000, inclusive.

The reactive biscyclobutarene oligomers exist as a mixture of oligomers wherein the value of the subscript n for each component of the mixture varies over a wide range. The average value of the subscript n for an oligomer prepared by the method of this invention is determined by the relative proportions of amino-substituted cyclobutarene and diamine employed in the reaction.

In another embodiment of this invention, two or more diamines are initially reacted and then oxidatively coupled with an amino-substituted cyclobutarene. A reactive biscyclobutarene oligomer having an unsymmetrical divalent bridging member can thus be prepared. A biscyclobutarene having an unsymmetrical bridging member may be easier to process than a biscyclobutarene having a symmetrical bridging member (symmetry may cause crystallization which makes the melting of the monomer or oligomer more difficult).

The biscyclobutarene monomers and reactive oligomers of this invention can be subjected to ring scission polymerization conditions to prepare highly crosslinked, three-dimensional polymeric networks that are thermoxidatively stable at high temperatures for prolonged time periods. In preferred embodiments, the prepared polymers exhibit no more than a 5 weight percent loss after exposure in air at 320° C. for 70 hours. In this context, "ring scission polymerization" refers to the reaction of an opened cyclobutane ring on a cyclobutarene moiety with either another opened cyclomethods.

The monomers and oligomers of this invention can be copolymerized with other monomers and reactive oligomers having at least one cyclobutarene-reactive functionality. Advantageously, the comonomer or oligomer chosen will copolymerize with the monomers and oligomers of this invention to form thermooxidatively stable copolymer compositions. Preferred comonomers and oligomers are maleimides, olefins, acetylenes, cyanates, and those having at least one cyclobutarene moiety as described in U.S. Pat. No. 4,540,763 and copending U.S. application Ser. No. 835,013, filed Feb. 28, 1986.

The following examples illustrate but do not limit the scope of this invention.

EXAMPLE 1

Preparation of a Biscyclobutarene Monomer With a Divalent Bridging Member Having a Diaryl-Substituted Azo Linkage

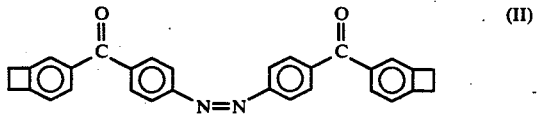

(II)

A solution of 0.7 grams (g) (7.07×10$^{-3}$ mols) of anhydrous cuprous chloride in 50 milliliters (ml) of dry pyridine is charged to a 100 ml resin pot equipped with an air sparge tube, a thermometer and a reflux condensor. Air is bubbled through the catalyst solution for 30 minutes. After 30 minutes, 2.0 g ($8.97 \times 10^{-3}$ mols) of the amino-substituted cyclobutarene disclosed as formula III is added to the reaction mixture while sparging is continued. The reaction mixture is heated to 60° C. and is sparged with air for 7 hours. After 7 hours the reaction mixture is allowed to cool and is then poured into 200 ml of water. 150 Milliliters of methylene chloride are added to the reaction mixture and the aqueous phase is extracted. An additional 150 ml of methylene chloride is added to the remaining reaction mixture and again the remaining aqueous phase is extracted. The combined methylene chloride solutions are washed with 10 percent hydrochloric acid ($3 \times 100$ ml) and water ($3 \times 100$ ml). The solution is then dried over anhydrous magnesium sulfate, filtered and evaporated in vacuo to yield a brown-red solid. This solid is chromatographed on a silica thin-layered chromatography plate eluting with a 10 percent ethyl acetate solution in toluene. The solid is further purified with a Chromatotron (Harrison Research, Model 7924T) to yield a red crystalline solid. This solid is further purified by recrystallization from a mixture of ethyl acetate and ethanol to yield 0.660 g of a red crystalline product with a melting point between 218° and 219° C.

EXAMPLE 2

Preparation of the Polymer From the Biscyclobutarene Monomer of Example 1

120 Milligrams of the monomer prepared from Example 1 is placed in a glass tube under a nitrogen atmosphere. A Woods metal bath is heated to 170° C. and the glass tube containing the monomer is placed in the bath. The monomer is subjected to the following temperatures for the following time periods.

| Temperature (°C.) | Time (Hour) |
|---|---|
| 220 | 1 |
| 235 | 1 |
| 250 | 1 |
| 270 | 1 |

After 1 hour at 270° C., the tube is removed from the bath and is cooled to room temperature under a nitrogen atmosphere. The pellet of polymer is removed from the bottom of the tube and is analyzed by thermogravimetric analysis to determine the thermoxidative stability of the polymer at isothermal conditions. The data is obtained using a DuPont Model 951 Thermogravimetric Analyzer with an air flow rate of 50 cubic centimeters per minute, interfaced with a duPont Model 9900 Computer/Thermoanalyzer.

Figure 2:
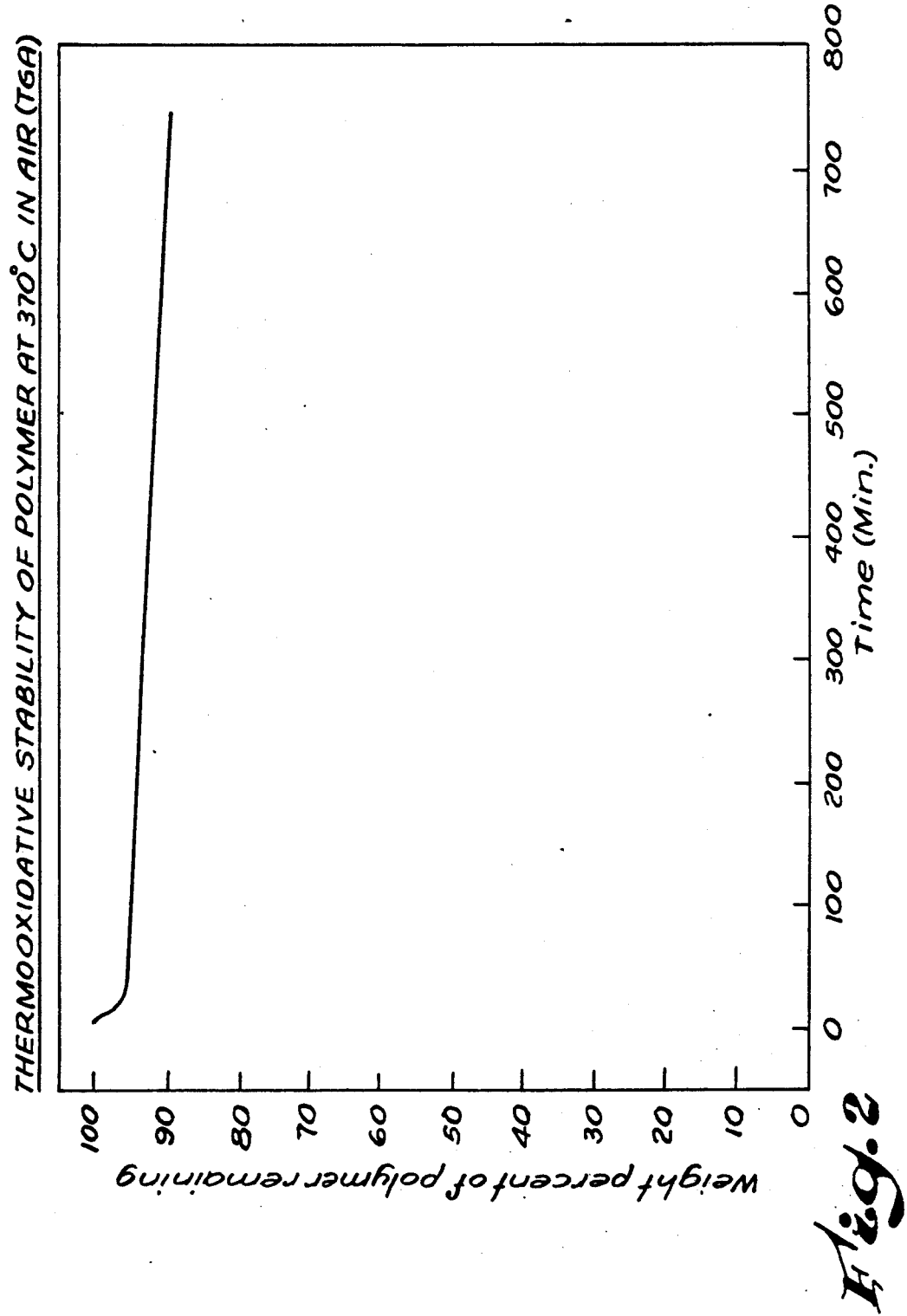

For a first run, a sample of the polymer is heated in the analyzer to 280° C. at 20° C. per minute, then the sample is heated to 310° C. at 10° C. per minute, and finally it is heated to 320° C. at 5° C. per minute. The temperature is then held at 320° C. for 4000 minutes. For a second run, a sample of the polymer is heated in the analyzer to 300° C. at 20° C. per minute, then the sample is heated to 340° C. at 10° C. per minute, and finally it is heated to 370° C. at 5° C. per minute. The temperature is then held at 370° C. for 720 minutes. The resulting isothermal weight loss for each of the two runs is presented in FIGS. 1 and 2.

The results of the first run indicate that about 93 percent of the weight of the polymer remains after exposure in air at 320° C. for 4000 minutes. The results of the second run indicate that 89 percent of the weight of the polymer remains after exposure in air at 370° C. for 720 minutes. These results indicate that a biscyclobutarene monomer having divalent bridging members with azo linkages exhibits outstanding thermooxidative stability at high temperatures for prolonged time periods.

Example 3

Preparation of a Reactive Biscyclobutarene Oligomer Having a Divalent Bridging Member with a Diaryl-Substituted Azo Linkage

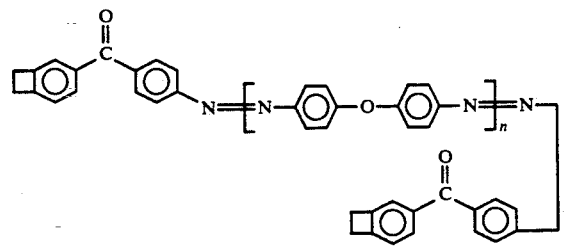

wherein n is an integer of 1 or more.

A solution of 0.18 g of anhydrous cuprous chloride and 50 ml of dry N,N-dimethylacetamide is mechanically stirred in a 100 ml resin pot equipped with an air sparge tube, a gas outlet, and an addition port. The catalyst solution is sparged with air while stirring at room temperature for 2½ hours. After 2½ hours, a mixture of 0.25 g ($1/12 \times 10^{-3}$ moles) of the amino-substituted cyclobutarene disclosed as formula III and 1.79 g ($8.96 \times 10^{-3}$ moles) of oxydianiline are added to the catalyst solution while sparging is continued. The mixture is sparged with air and stirred for 16 hours, after which it is poured into 200 ml of water. The resulting black precipatate is collected by filtration, washed with water and is dried in a vacuum oven at 80° C. for 3 hours. A yield of 2.00 g of a black solid is obtained. When this solid is polymerized in a manner similar to the polymerization of the monomer in Example 2, and the polymer is analyzed for its thermooxidative stability similar to the procedure described in Example 3, the polymer exhibits outstanding thermooxidative stability at high temperatures for prolonged time periods.

What is claimed is:

1. A biscyclobutarene monomer having two cyclobutarene moieties bridged by a divalent radical having at least one azo linkage.

2. The biscyclobutarene monomer of claim 1 of the formula:

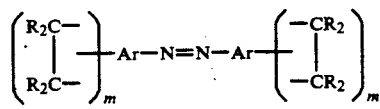

wherein
Ar is an aromatic moiety having one valence on each of two adjacent carbon atoms of an aromatic ring;
each R is independently hydrogen, a monovalent electron-donating moiety, or a monovalent electron-withdrawing moiety; and m is an integer of 1 or 2.

3. The biscyclobutarene monomer of claim 2 of the formula:

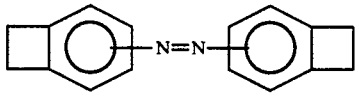

4. The biscyclobutarene monomer of claim 1 wherein the azo linkage is a diarylene-substituted azo linkage.

5. The biscyclobutarene monomer of claim 4 of the formula:

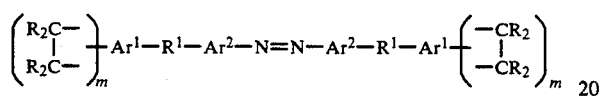

wherein
- $Ar^1$ is an aromatic moiety having one valence on each of two adjacent carbon atoms of an aromatic ring;
- $Ar^2$ is arylene;
- each R is independently hydrogen, a monovalent electron-donating moiety, or a monovalent electron-withdrawing moiety;
- $R^1$ is a direct bond, oxygen, sulfur, sulfinyl, sulfonyl, carbonyl, vinylene, ethynylene, oxycarbonyl, aminocarbonyl, or fluoroalkylene; and
- m is an integer of 1 or 2.

6. The biscyclobutarene monomer of claim 5 of the formula:

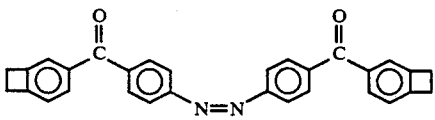

* * * * *